United States Patent [19]

Cullen et al.

[11] Patent Number: 5,494,820
[45] Date of Patent: Feb. 27, 1996

[54] *STREPTOMYCES BRAEGENSIS* STRAIN AND ITS CULTIVATION IN A PROCESS FOR PRODUCING $C_9$-DESOXO-FK-520.

[75] Inventors: Walter P. Cullen, East Lyme; Mark A. Guadliana, Stonington; Liang H. Huang, East Lyme, all of Conn.; Keiji Kaneda, Chita; Nakao Kojima, Nagoya, both of Japan; Gloria Kostek, Preston, Conn.; Satoshi Nishiyama, Chita, Japan; Yuji Yamauchi, Handa, Japan; Yasuhiro Kojima, Nishio, Japan

[73] Assignee: Pfizer Inc., New York, N.Y.

[21] Appl. No.: 129,159

[22] PCT Filed: Mar. 27, 1992

[86] PCT No.: PCT/US92/02324

§ 371 Date: Jan. 24, 1994

§ 102(e) Date: Jan. 24, 1994

[87] PCT Pub. No.: WO92/18506

PCT Pub. Date: Oct. 29, 1992

Related U.S. Application Data

[63] Continuation of Ser. No. 683,639, Apr. 11, 1991, abandoned.

[51] Int. Cl.⁶ .............................. C12P 1/04; C12P 17/18
[52] U.S. Cl. .................. 435/253.5; 435/119; 435/118
[58] Field of Search ................................. 435/119, 118, 435/886, 253.5

[56] References Cited

U.S. PATENT DOCUMENTS 4,404,190  9/1983  Dolak ....................................... 424/118

FOREIGN PATENT DOCUMENTS 323865  7/1989  European Pat. Off. .
402931  12/1990  European Pat. Off. .

OTHER PUBLICATIONS

Hatanaka et al, *J. Antibiot.*, vol. 41, 1988 pp. 1592–1601.
Hatanaka et al, *J. Antibiot*, vol. 42, 1989 pp. 620–622.
Rance et al, *J. Antibiot.*, vol. 42, 1989 pp. 206–217.

*Primary Examiner*—Irene Marx
*Attorney, Agent, or Firm*—Peter C. Richardson; Paul H. Ginsburg; Garth Butterfield

[57] ABSTRACT

A compound of the formula

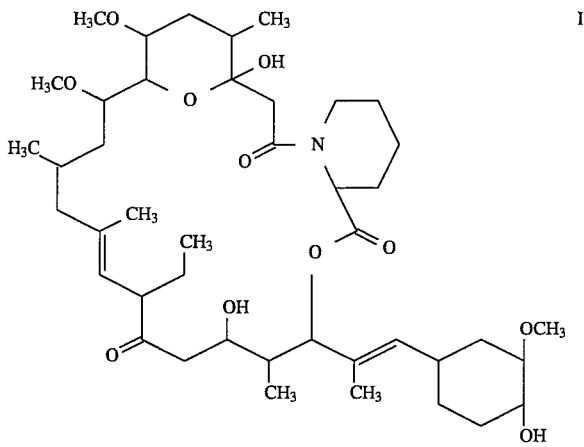

is a novel immunosuppressant agent prepared by fermenting *Steptomyces braeaensis* subsp. *pulcherrimus*, ATCC 55150, or another compound of the formula I producing strain and extracting the compound of the formula I from the fermentation medium. The compound is useful in treating transplant rejection and autoimmune diseases.

7 Claims, 2 Drawing Sheets

STREPTOMYCES BRAEGENSIS STRAIN AND ITS CULTIVATION IN A PROCESS FOR PRODUCING C₉-DESOXO-FK-520.

This application was filed under 352/SC 371 as the national phase of PCT patent application PCT/US92/02324 which was a continuation of U.S. patent application 07/683,639 filed Apr. 11, 1991, now abandoned.

BACKGROUND OF THE INVENTION

This invention relates to a new macrocyclic lactone immunosuppressant agent, a process for its production and its use in a human host for treatment of autoimmune diseases and/or prevention of organ transplant rejections. This application is a continuation of U.S. application 683,639 first filed on Apr. 11, 1991. Priority is hereby claimed to that application. In 1983, the United States Food and Drug Administration licensed cyclosporin, an anti-rejection drug that revolutionized the field of organ transplant-surgery. The drug acts by inhibiting the body's immune system from mobilizing its vast arsenal of natural protecting agents to reject the transplant's foreign protein. Although cyclosporin is effective in fighting transplantation rejection, it suffers drawbacks in causing kidney failure, liver damage and ulcers which in many cases can be very severe. Newer, safer drugs exhibiting less side effects are constantly being searched for. European Patent Publication No. 0184162 of Fujisawa Pharmaceutical Co., Ltd., describes the macrolids immunosuppressants FK-506 and FK-520. The latter is produced by S. hygroscopicus subsp. yakushimaensis No. 7238. Other immunosuppressants are described in European Patent Application Publication Nos. 0323042, 0323865, 0356399 of Fisons plc, Merck & Co. Inc., and Sandoz, respectively.

SUMMARY OF THE INVENTION

The present invention relates to a new immunosuppressant of the formula

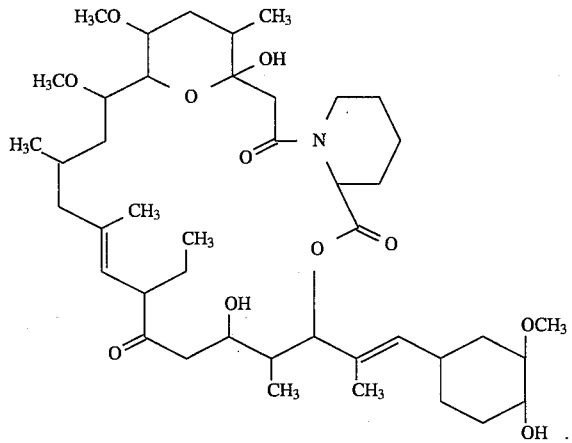

The compound of the formula I may be referred to as "C₉-desoxo-FK- 520" because it differs from FK-520 in lacking an oxo group at the C₉ position. In view of the compound's similarity to FK-520 its stereochemistry is expected to be as shown in the following formula

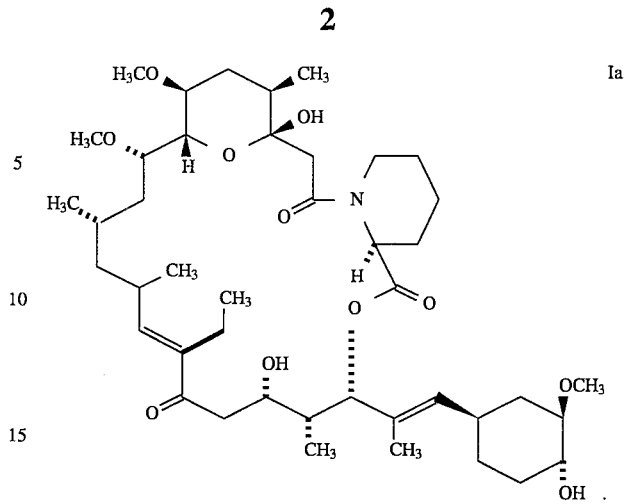

The present invention also relates to a process for preparing the compound of the formula I comprising fermenting a compound of the formula I producing strain of bacteria (e.g., a Streptomyces strain such as *Streptomyces braegensis* subsp. *pulcherrimus* Huang subsp. nov.) in an aqueous nutrient medium containing an assimilable carbon source and an assimilable nitrogen source, said fermentation being conducted preferably at a pH between about 4.0 and about 8.0, and extracting the compound of the formula I from the medium, preferably at a pH of about 4.0 to about 8.0.

The present invention also relates to a pharmaceutical composition containing an amount of the compound of the formula I effective in treating autoimmune disease (e.g. rheumatoid arthritis) or preventing organ transplant rejection in a mammal (e.g. a human) in combination with a pharmaceutically acceptable carrier.

The present invention also relates to a method of treating a mammal (e.g. a human) to prevent transplantation rejection or treating an autoimmune disease (e.g. rheumatoid arthritis) in a mammal (e.g. a human) comprising administering to said mammal a therapeutically effective amount of the compound of the formula I.

Finally, the present invention is directed to a biologically pure culture having the characteristics of *Streptomyces braegensis* subsp. *pulcherrimus* Huang subsp. nov., ATCC 55150, and ATCC 55150 per se, as well as mutants and transformants of any of the foregoing capable of producing the compounds of the formula I, including any such culture in freeze-dried form. Such a culture is capable of producing the compound of the formula I in a recoverable quantity upon fermentation in an aqueous nutrient medium comprising assimilable sources of carbon and nitrogen.

DETAILED DESCRIPTION OF THE INVENTION

Figure 1:
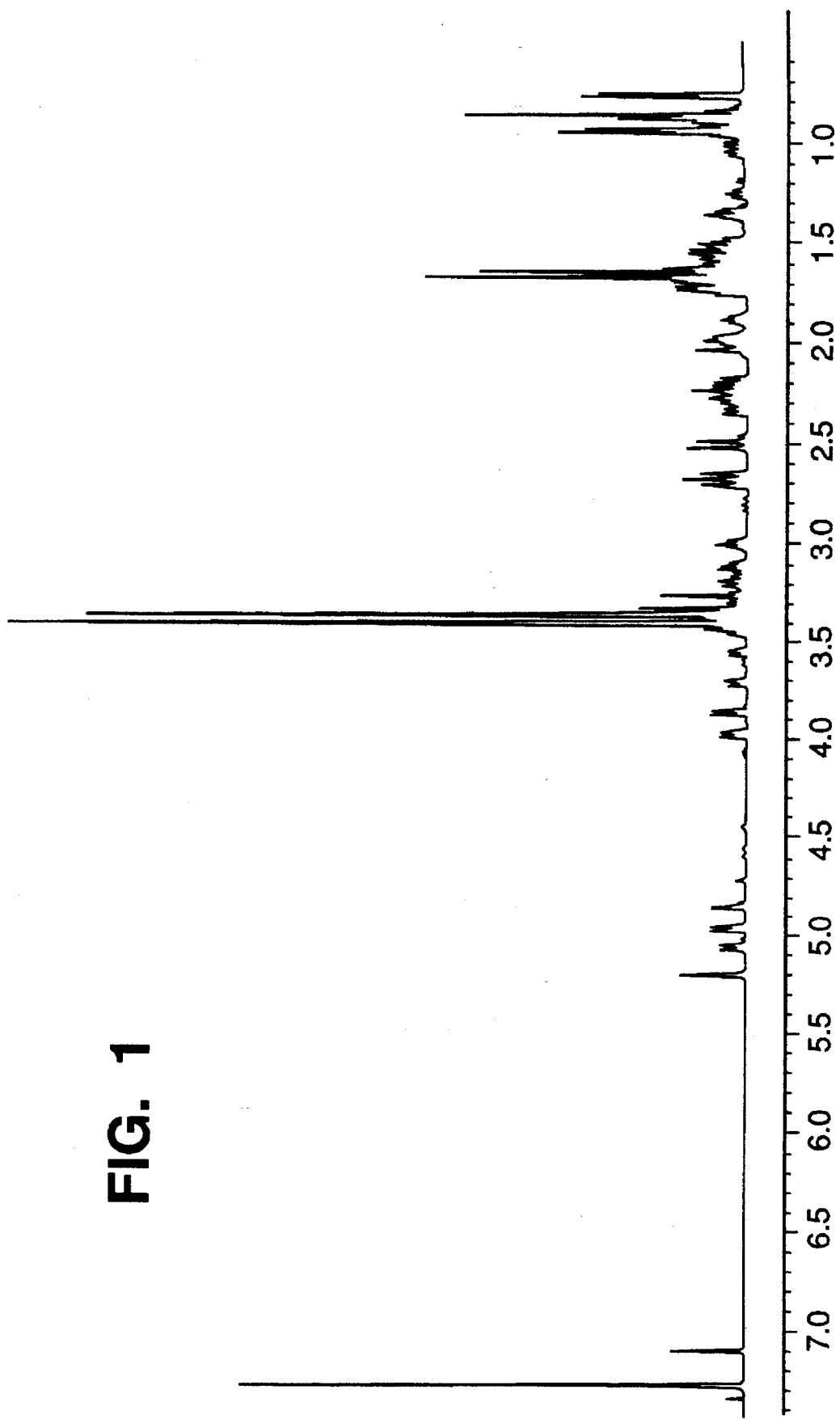
FIG. 1 is the proton NMR spectrum in CDCl₃ of the compound of the formula I, C₉-desoxo-FK-520.

In general, the compound of the formula I can be produced by culturing a compound of the formula I producing strain of bacteria in an aqueous nutrient medium containing sources of assimilable carbon and nitrogen, preferably under submerged aerobic conditions (e.g. shaking culture, submerged culture, etc.). The aqueous medium is preferably maintained at a pH of about 4.0 to about 8.0 throughout the fermentation process. A higher pH may lead to loss of product. The desired pH may be maintained by the use of appropriate buffering agents.

A preferred culture for producing the compound of the formula I is designated *Streptomyces braegensis* subsp. *pulcherrimus* Huang subsp. nov., and has been deposited in The American Type Culture Collection, Rockville, Md. under their accession number ATCC 55150.

This novel culture was derived from a soil sample collected in Misumitown, Yamaguchi prefecture, Japan, and identified in the culture collection of Pfizer Inc as N927-101. Its single colony isolate is identified as N927-101-SC 50. Its description and classification were provided by Dr. L. H. Huang.

The cultures were found to produce narrow hyphae of the Actinomycetales, an unfragmented substrate mycelium, and an aerial mycelium on which spore chains are produced. The results of whole-cell analysis further indicates their belonging to the genus Streptomyces. The $C_9$-desoxo-FK-520 producing strain of a *Streptomyces braegensis* subsp. *pulcherrimus* Huang subsp. Nov., Streptomyces species, isolated from soil samples in Misumitown, Yamaguchi prefecture, Japan, is identified in the culture collection of Pfizer Inc. as N927- 101. Its single colony isolate, identified as N927-101-SC50 has been deposited with the American Type Culture Collection, 12307 Parklane Drive, Rockville, Md., 20852 and has received Accession No. 55150.

Each of culture N927-101 and culture N927-101SC50 was planted from a slant into ATCC #172 broth and grown for four days at 28° C. on a shaker. It was then centrifuged for 20 minutes, washed three times with sterile water and planted on media commonly used for identification of members of the Actinomycetales.

The cultures were incubated at 28° C. and the results were read at varying times but most commonly were taken at 14 days. The colors were described in common terminology, but exact colors were determined by comparisons with color chips from the *Color Harmony Manual*, fourth edition. The methods of whole-cell amino acid and sugar analyses are those described in B. Becker et al., *Appl. Microbiol.*, 12, 421–423 (1964); and in M. P. Lechevalier, *J. Lab. Clin. Med.*, 71, 934–944 (1968 ). For comparison purposes, the type strains of *Streptomyces tsukubaensis* BP-927, *S. hygroscopicus* subsp. *yakushimaensis* BP-928, *S. nigrescens* ATCC 23941, *S. braegensis* NRRL 12567, and *S. braegensis* subsp. *japonicus* N617-29 were used.

Identification media used for the characterization of the cultures and references for their composition are as follows:

1. Tryptone-Yeast Extract Broth—(ISP #1 medium, Difco).

2. Yeast Extract-Malt Extract Agar—( ISP #2 medium, Difco).

3. Oatmeal Agar—(ISP #3 medium, Difco).

4. Inorganic Salts-Starch Agar—(ISP #4 medium, Difco).

5. Glycerol-Asparagine Agar—(ISP #5 medium, Difco).

6. Peptone-Yeast Extract Iron Agar—(ISP #6 medium, Difco).

7. Czapek-Sucrose Agar—S. A. Waksman, *The Actinomycetes*, Vol. 2, medium no. 1, p. 328, (1961).

8. Glucose-Asparagine Agar—Ibid, medium no. 2, p. 328.

9. Bennett's Agar—Ibid, medium no. 30, p. 331.

10. Emerson's Agar—Ibid, medium no. 28, p. 331.

11. Nutrient Agar—Ibid, medium no. 14, p. 330.

12. Gordon and Smith's Tyrosine Agar—R. E. Gordon and M. M. Smith, *J. Bacteriol.*, 69, 147–150 (1955).

13. Casein Agar—Ibid.

14. Calcium Malate Agar—S. A. Waksman, *Bacteriol. Rev.*, 21, 1–29 (1957).

15. Gelatin—R. E. Gordon and J. M. Mihm, *J. Bacteriol.*, 73, 15–27 (1957).

16. Starch—Ibid.

17. Organic Nitrate Broth—Ibid.

18. Dextrose Nitrate Broth—S. A. Waksman, *The Actinomycetes*, Vol. 2, medium no. 1, p. 328 ( 1961), with 3 g dextrose substituted for 30 g sucrose and agar omitted.

19. Potato Carrot agar—M. P. Lechevalier, *J. Lab. and Clinical Med.*, 71, 934–944 (1968), but use only 30 g potatoes, 2.5 g carrots and 20 g agar.

20. 2% Tap Water Agar.

21. Skim Milk—Difco.

22. Cellulose utilization— a) H. L. Jensen, *Proc. Linn. Soc. N.S.W.*, 55, 231–248 (1930)

b) M. Levine and H. W. Schoenlein, *A Compilation of Culture Media*, medium no. 2511 (1930).

23. Carbohydrate Utilization—(ISP #9 medium, Difco).

24. Temperature Range—ATCC 172 medium in ATCC Media Handbook, 1st Ed., p. 10 (1984).

The cultural characteristics of culture N927-101SC50, which produced higher titers of the compound of the formula I than culture N927-101, are as follows:

Yeast Extract-Malt Extract Agar

Growth good; white, pale gray, pale pink-gray to pink-gray (near gray series 3 dc, 5 dc, 5 fe); raised; smooth, granular to wrinkled; aerial mycelium same as surface; reverse yellowish to dark brown (2 ic, 4 ni, 4 li); no soluble pigment.

Oatmeal Agar

Growth moderate to good; white, pale gray to gray (near gray series 3 dc, 3 fe); slightly raised, smooth to granular, aerial mycelium same as surface; reverse gray to pink-gray (near gray series 3 fe, 5 fe, 7 ih); soluble pigment pink-gray (near gray series 5 dc).

Inorganic Salts-Starch Agar

Growth moderate to good; white, pale gray, gray to pink-gray (near gray series 3 dc, 3 fe, 5 fe); raised, smooth to wrinkled, aerial mycelium same as surface; reverse purplish black (near gray series 7 ml); soluble pigment yellowish brown to pink (3 gc, 6 ca).

Glycerol-Asparagine Agar

Growth poor to moderate; white, cream, pale gray to gray (2 ca, near gray series 3 dc, 3 fe); appearing as isolated colonies, thin to slightly raised, smooth to granular; aerial mycelium white, pale gray to gray; reverse cream to yellowish (2 ca, 2 nc, 2 pe); no soluble pigment.

Czapek-Sucrose Agar

Growth poor to moderate, pale gray to gray (near gray series 3 dc, 3 fe, 5 ih); thin to slightly raised, smooth to granular, aerial mycelium same as surface; reverse colorless, pale gray to gray (near gray series 3 dc, 3 fe); no soluble pigment.

Glucose-Asparagine Agar

Growth moderate; yellow, gray to pink-gray (2 ic, near gray series 3 fe, 7 ih); appearing as isolated colonies; smooth, wrinkled to granular; aerial mycelium gray to pink-gray; reverse pink-gray (near gray series 7 ih); soluble pigment none to pale pink (4 ca).

Gordon and Smith's Tyrosine Agar

Growth moderate, brown (4 le); slightly raised, smooth to slightly granular; aerial mycelium sparse, white to pale gray (near gray series 3 dc); reverse brown (3 ic, 4 lc); soluble pigment yellowish brown (3 nc).

Casein Agar

Growth good; white, grayish yellow to lavender (2 gc, 4 ge); raised, smooth to wrinkled, aerial mycelium white; reverse yellowish to lavender (2 ga, 2 ic, 4 ge); soluble pigment yellowish brown (3 lc).

Bennett's Agar

Growth excellent; white, pale gray to gray (near gray series 3 dc, 3 fe); highly raided; smooth, slightly wrinkled to granular; aerial mycelium same as surface; reverse pink-gray to dark pink-gray (near gray series 7 ih, 7 ml); soluble pigment yellowish (2 ga).

Emerson's Agar

Growth good, tan to pink (near 3 gc, 5 ea); raised, slightly wrinkled, no aerial mycelium; reverse brown (3 ie); soluble pigment yellowish brown (3 lc).

Nutrient Agar

Growth moderate; white, pale pink-gray to pink-gray (near gray series 5 ic, 5 fe); appearing as isolated colonies, moderately raised, smooth to wrinkled; aerial mycelium same as surface; reverse yellowish to brown (2 ga, 2 ic, 4 ie); no soluble pigment.

Calcium Malate Agar

Growth scant, pale gray to gray (near gray series 3 dc, 3 fe); slightly raised, thin, smooth, aerial mycelium same as surface; reverse same as surface; no soluble pigment.

Potato Carrot Agar

Growth moderate, pink-gray to dark pink-gray (near gray series 5 ih, 5 ml), appearing as isolated colonies, slightly raised, smooth, aerial mycelium same as surface; reverse same as surface; no soluble pigment.

Tap Water Agar

Growth poor; pale gray, gray to pink-gray (near gray series 3 dc, 3 fe, 7 ih); thin, smooth; aerial mycelium same as surface; reverse pale gray to gray (near gray series 3 dc, 3 fe); no soluble pigment.

Gelatin Agar

Growth moderate to good; white to brown (3 le), but pale yellowish brown (3 gc) at edge; moderately raised; smooth, granular to slightly wrinkled; aerial mycelium white; reverse brown to dark brown (4 ie, 4 pi, 4 ni); no soluble pigment.

Starch Agar

Growth moderate to good; white, pale gray, gray, brown to dark brown (4 ie, 4 nl, near gray series 3 dc, 3 fe); moderately raised, smooth to granular; aerial mycelium same as surface; reverse brown to dark brown (4 lg, 4 li); soluble pigment yellowish (2 lc).

Morphological Properties

The morphological observations were made on oatmeal agar after 15 days of incubation: spore mass in Gray color-series; spore chains in Section Spirales, tightly coiled or slightly open or coiled into an irregular mass, of small diameter (3–4 μm), 3–8 turns per spore chain, may aggregate into a hygroscopic mass, 10 to 50 spores per spore chain; sporophores monopodially branched; spores short-rod shaped to rod shaped, sometimes globose, oval to elliptical, straight, but sometimes slightly curved, often with both ends not parallel to each other, 0.9–1.8× 0.8–1.1 μm or 0.9–1.2 μm diam.; smooth to warty with a rugose surface, as revealed by scanning electron microscopy.

Biochemical Properties

Melanin not produced; hydrogen sulfide produced; gelatin liquefied; starch hydrolyzed; nitrate not reduced to nitrite; good growth but no decomposition on both cellulose broths; clearing but no coagulation on milk; casein digestion positive; tyrosine digestion positive; calcium malate digestion negative. Carbohydrate utilization: Glucose, fructose, inositol, mannitol, raffinose, sucrose, and xylose utilized; arabinose and rhamnose not utilized.

| Temperature Relations - | | | |
|---|---|---|---|
| 21° C. | 28 ° C. | 37° C. | 45° C. |
| Moderate Growth | Excellent Growth | Good Growth | No Growth |

Cell Wall Analysis

The whole-cell hydrolysates contained LL-diaminopimelic acid and galactose.

The culture N927-101SC50 is characterized by the gray spores in mass, the negative melanin reaction, the spiral spore chains, and the smooth to warty spores. The whole cell hydrolysates indicate the presence of LL-diaminopimelic acid and galacross. Glucose, fructose, inositol, mannitol, raffinose, sucrose, and xylose were utilized; but arabinose and rhamnose were not utilized. Therefore, the culture belongs to the genus Streptomyces.

The parent culture N927-101 resembles culture N927-101SC50 in all of the biochemical properties and temperature range except for minor differences in culture characteristics. On yeast extract-malt extract agar, culture N927-101 produced dark purple rather than yellow to dark brown colony reverse and purple rather than no soluble pigment. It sporulated better than N927-101SC50 on inorganic salts-starch agar, starch agar, and gelatin agar, but worse on nutrient agar. Although the black hygroscopic patches in culture N927-101SC50 were not as obvious as in culture N927-101 at 15 days of incubation, almost all of the colonies of both cultures have turned black on the following agars after six weeks of incubation: yeast extract-malt extract agar, oatmeal agar, inorganic salts-starch agar, Czapek-sucrose agar, Bennett's agar, potato carrot agar, and tap water agar. Thus, it is concluded that culture N927- 101SC50, which is a natural isolate of culture N927-101, is the same as culture N927-101.

When culture N927-101SC50 was compared with FK-506 producing culture *S. tsukubaensis* BP-927 and FK-520 and FK- 523 producing culture *S. hygroscopicus* subsp. *yakushimaensis* BP-928 (available from the Fermentation Research Institute in Japan), the differences are apparent (Table 1). In addition, culture *S. tsukubaensis* produced an orange tint of soluble pigment on yeast extract-malt extract agar, oatmeal agar, and glucose-asparagine agar; whereas *S. hygroscopicus* subsp. *yakushimaensis* produced no distinct soluble pigment. On yeast extract-malt extract agar, and inorganic salts-starch agar, the colony reverse was brown and gray-pink, respectively, for *S. tsukubaensis,* but was gray to dark gray and yellow-gray to black for *S. hygroscopicus* subsp. *yakushimaensis.*

When compared with known species of Streptomyces, the culture N927-1018C50 closely resembles *Streptomyces braegensis* Dietz NRRL 12567 (U.S. Pat. No. 4,404,190, Sep. 13, 1983), *S. braegaensis* Dietz subsp. *japonicus* Huang N617-29 (Rance, M. J. et al., *J. Antibiot.,* 42, 206–217 (1989)), and *S. nigrescens* (Sveshnikova) Pridham et al. ATCC 23941 (Shirling, E. B. and D. Gottlieb, *Int. J. Syst. Bacteriol,* 18, 279–396 (1968)). These three cultures were grown for comparisons.

Culture N927-101SC50 is similar to *S. nigrescens* in most of the biochemical properties except that the former, but not the latter, produced hydrogen sulfide and showed a better growth on cellulose broth. *S. nigrescens,* unlike culture N927-101SC50, showed no distinct soluble pigment and no distinct pigment on colony reverse. The colors of colony reverse ranged from yellow, yellow-gray, and gray to sometimes black.

Culture N927-101SC50 is similar to *S. braegensis* subsp. *japonicus* in almost all of the biochemical properties except for its ability to produce hydrogen sulfide. Generally, *S. braegensis* subsp. *japonicus* did not produce distinct soluble pigment. Its colony reverse varied from yellow, gray-brown, and gray-yellow-brown to dark brown.

Culture N927-101SC50 has the same biochemical properties as *S. braegensis* except for its ability to produce hydrogen sulfide and better growth in cellulose broth. The colony reverse of the latter was pale pink, reddish pink, and reddish on glucose-asparagine agar, Bennett's agar, and starch agar, respectively; but on these three media the former had a pink-gray to brown colony reverse. On yeast extract-malt extract agar, inorganic salts-starch agar and casein agar, the former had a purple colony reverse; but the latter had a yellow-brown, pale gray to brown, and pale yellowish colony reverse, respectively. Culture N927-101SC50 produced pink-gray but not pale yellow-brown soluble pigment on oatmeal agar, and yellow brown to pink but not cream to yellow-brown soluble pigment on inorganic salts-starch agar.

On the basis of the above results, it is concluded that the culture N927-101SC50 represents a new subspecies of *S. braegensis* and is designated *Streptomyces braegensis* subsp. *pulcherrimus* Huang subsp. nov. The subspecific epithet (L. adj., *pulcherrimus,* prettiest) refers to the beauty of a purple pigment produced on some solid media and in ATCC 172 broth. It has been deposited at the American Type Culture Collection under the accession number 55150.

TABLE 1

Comparisons of N927-101SC50 with *S. tsukubaensis* and *S. hygroscopicus* subsp. *yakushimaensis*

| Properties | N927-101SC50 | *S. tsukubaensis* BP927 | *S. hygroscopicus* subsp. *yakushimaensis* BP-928 |
|---|---|---|---|
| Compound produced | Compound of formula I | FK-506 | FK-520 FK-523 |
| Spore color in mass | Gray | Gray or Red | Gray |
| Spore chains | spiral | straight | spiral |
| Spore Surface | smooth to rugose | smooth | rugose |
| Growth in L & S cellulose broth | + | – | – |
| Degradation of tyrosine | + | – | + |
| Coagulation of milk Utilization | – | + | + |
| Arabinose | – | – | + |
| Fructose | + | – | + |
| Mannitol | + | – | + |
| Raffinose | + | – | – |
| Rhamnose | – | + | – |

The Streptomyces culture used to produce the compound of formula I (e.g., N927-101 or N927-101SC50) is preferably grown at a temperature from about 20° C. to about 40° C. more preferably from about 24° C. to about 36° C., under submerged conditions with agitation and aeration in a medium consisting of a carbon source, a nitrogen source, one or more mineral salts containing trace elements such as iron, cobalt, copper, zinc etc., and one or more buffering agents. The compound can be recovered by extracting the whole broth with an organic solvent (e.g., n-butanol, methyl isobutyl ketone, ethyl acetate or chloroform), preferably at a pH of about 4.0 to about 8.0. Alternatively, after growth has been completed, the mycelium may be separated and extracted with an organic solvent (e.g., acetone or methanol) as described above, and the liltrate discarded. The solvent is concentrated to a thin syrup, triturated with an organic solvent (e.g., heptane) and then chromatographed (e.g., on silica gel) to obtain the pure compound.

The preferred sources of carbon in the nutrient medium are carbohydrates such as glucose, xylose, galactose, glycerin, starch, dextrin, maltose, rhamnose, raffinose, arabinose, mannose, and salicin. Other sources which may be included are corn steep liquor, grain solubles, fish meal and cotton seed meal.

The preferred sources of nitrogen are yeast extract, meat extract, fish meal peptone, gluten meal, cottonseed meal, soybean meal and other vegetable meals (partially or totally defatted), casein hydrolysates, yeast hydrolysates, corn steep liquor, dried yeast, wheat germ, feather meal, peanut powder, distillers solubles as well as inorganic and organic nitrogen compounds such as ammonium salts (e.g. ammonium nitrate, ammonium sulfate, ammonium phosphate, etc.), urea and amino acids (e.g., casamino acids).

The preferred buffering agents are calcium carbonate or phosphates. Other suitable buffering agents include morpholinoethanesulfonic acid (MES) and morpholinopropanesulfonic acid (MPS). Various nutrient materials may be used which inherently possess buffering properties.

The carbon and-nitrogen sources, though advantageously employed in combination, need not be used in their pure form. Less pure materials, which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, iron salts, zinc salts, cobalt salts, and the like. If necessary, especially when the culture medium foams, a defoaming agent, such as liquid paraffin, fatty oil, plant oil, mineral oil or silicone may be added.

Submerged aerobic cultural conditions are preferred for producing large amounts of the compound of the formula I. For the production of the compound of the formula I in small amounts, a shaking or surface culture in a flask or bottle is employed. When fermentation is carried out in large tanks, it is preferable to use the vegetative form of the organism for inoculation in the production tanks in order to avoid growth lag in the process of production of the compound of the formula I. Accordingly, it is desirable first to produce a vegetative inoculum of the organism by inoculating a relatively small quantity of culture medium with spores of roycelia of the organism produced in a "slant" and culturing said inoculated medium, also called the "seed medium", and then to transfer the cultured vegetative inoculum aseptically to large tanks. The fermentation medium, in which the vegetative inoculum is produced, may be substantially the same as or different from the medium utilized for the production of the compound of the formula I and is generally autoclaved to sterilize the medium prior to inoculation. The pH of the medium is generally adjusted to below 8.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor by various pumping equipment or by the passage of sterile air through the medium. Aeration may be effected by passing sterile air through the fermentation mixture.

The fermentation is usually conducted at a temperature between about 20° C. and about 40° C., preferably about 24° C. to about 36° C., for a period of about 50 hours to about 150 hours, which may be varied according to fermentation conditions and scales. Preferably, the production cultures are incubated for about 96 hours at 27° C. on a rotary shaker operating at 220 rpm, wherein the pH of the fermentation medium is preferably maintained at a pH of about 4.0 to about 8.0, more preferably about 6.0 to about 8.0, to harvest.

Culturing/production media that may be used for carrying out the fermentation include the following:

Medium A: glycerol, corn starch, cerelose, cotton seed meal, torula yeast, corn steep liquor, calcium carbonate and cobalt chloride, in preferred weight percentages of the fermentation medium, respectively, of: 1.0%, 1.0%, 0.5%, 1.0%, 0.5%, 0.5%, 0.2%, and 0.0005% and 0.2% (volume/volume) of an antifoam agent such as P-2000 (Dow Corning (Trademark)). The pH of this medium is generally adjusted to about 6.3 to about 6.5 prior to autoclaving and inoculation.

Medium B: corn starch, corn steep liquor, torula yeast, magnesium sulfate, potassium dibasic phosphate, cobalt chloride and calcium carbonate, in preferred weight percentages of the fermentation medium, respectively, of: 4.5%, 1.0%, 1.0%, 0.01%, 0.01% and 0.0001%, and 0.2% (volume/volume) of an antifoam agent such as P-2000 (Dow Corning (trademark)). The pH of this medium is generally adjusted to about 7.0 to about 7.2 prior to autoclaving and inoculation.

Medium C: cerelose, soybean meal, ammonium sulfate, potassium dibasic phosphate, calcium carbonate, NZ amine YTT (Sheffield (trademark)) and cobalt chloride in preferred weight percentages of the fermentation medium, respectively, of: 2.0%, 3.0%, 0.5%, 0.5%, 0.3%, 0.5% and 0.0005% and 0.2% (volume/volume) of an antifoam agent such as P-2000 (Dow Corning (trademark)). The pH of this medium is generally adjusted to about 7.0 to about 7.2 prior to autoclaving and inoculation.

The produced compound of the formula I can be recovered from the culture medium by conventional means which are commonly used for the recovery of the other known biologically active substances. The compound of the formula I produced is found in the cultured mycelium and filtrate, and accordingly can be isolated and purified from the mycelium and the liltrate. The mycelium can be separated, by filtering or centrifuging the cultured broth. The mycelium can then be extracted with a conventional solvent, such as methanol or acetone, separated and concentrated. Treatment of the concentrate with a conventional resin (e.g., anion or cation exchange resin, non-ionic adsorption resin, etc.), treatment with a conventional adsorbent (e.g., activated charcoal, silic acid, silica gel, cellulose, florisil, alumina, etc.), crystallization, and recrystallization are then performed to recover the desired compound.

In a preferred method for preparing the compound of the formula I, inoculum is prepared by scraping vegetative cells from slants or Roux bottles inoculated with the N927-101 culture. A solid medium suitable for initial growth on slants and Roux bottles is ATCC medium 172 described below:

| Ingredient | Grams/liter |
| --- | --- |
| Glucose | 10 |
| Soluble starch | 20 |
| Yeast extract | 5 |
| NZ Amine A | 5 |
| Calcium carbonate | 1 |
| Agar | 20 |
| Distilled water to 1000 ml; | |
| pH to 7.0 with KOH; | |

Vegetative cells from slants are used to inoculate either shake flasks or inoculum tanks; or alternatively the inoculum tanks are inoculated from shake flasks. In shake flasks, growth will generally have reached its maximum in 48 to 96 hours whereas in the inoculum tanks growth will usually be at the most favorable period in 72 to 120 hours. A fermenter is inoculated with vegetative broth from the inoculum flasks or tank under completely aseptic conditions and fermented for a period of 72 to 120 hours. Aeration is maintained in the shake flask by agitation on a shaker or in tanks by forcing sterile air through a sparger at the rate of ½ to 2 volume of air per volume of broth per minute. The speed of agitation (stirring) depends upon the type of agitator employed; a shake flask is usually run at 150 to 200 cycles per minute (cpm) and a fermenter at 300 to 1700 revolutions per minute (rpm). Sterility must be maintained at all times. The temperature is regulated between 24° C. and 36° C. Foaming during the fermentation can be controlled with sterile antifoams such as refined soybean oil, or other suitable antifoaming agents added to the makeup or to the fermenter aseptically as needed after inoculation.

Shake flasks are prepared using one of the following media:

| | Grams/Liter |
|---|---|
| ATCC 172 | |
| Glucose | 10 |
| Soluble starch | 20 |
| Yeast extract | 5 |
| NZ Amine A (Trademark of Quest International Norwich, New York) | 5 |
| Calcium Carbonate | 1 |
| | pH 7.0–7.1 |
| FK-506S | |
| Glycerol | 10 |
| Corn starch | 10 |
| Cerelose | 5 |
| Cotton seed meal | 10 |
| Torula yeast | 5 |
| Corn steep liquor | 5 |
| Calcium Carbonate | 2 |
| Cobalt Chloride | 0.005 |
| | pH to 6.3–6.5 |
| JDYTT | |
| Cerelose | 10 |
| Corn starch | 5 |
| NZ Amine YTT (Trademark of Quest International Norwich, New York) | 5 |
| Corn steep liquor | 5 |
| Calcium carbonate | 3 |
| Cobalt chloride | 0.005 |
| | pH to 6.5–6.7 |

One hundred ml of medium is distributed into 300 ml shake flasks and sterilized at 120° C. and 1.06 kg/cm² for 30 minutes. After cooling, the medium is inoculated with a vegetative cell suspension from the N927-101 slant culture grown on ATCC medium 172 in agar. The flasks are shaken at 28° C. on a shaker having a displacement of 2.5–3.8 cm to 5.0– 7.3 cm and 150 to 200 rpm for 2 to 4 days. Ten ml may be used to inoculate one 2.8 liter Fernbach flask containing 1 liter of media or 1 flask may be used to inoculate a 5 liter fermentation vessel containing 3 liters of 1 of the following media:

| FK-506-FM | Grams/Liter | ATCC 172 | Grams/Liter |
|---|---|---|---|
| Corn starch | 45 | Glucose | 10 |
| Corn steep liquor | 10 | Soluble starch | 20 |
| Torula yeast | 10 | Yeast extract | 5 |
| Magnesium sulfate | 0.1 | NZ Amine A | 5 |
| Potassium dibasic phosphate | 0.1 | Calcium carbonate | 1 |
| Cobalt chloride | 0.001 | | |
| Calcium carbonate | 2 | | |
| | pH to 7.0–7.2 | | |

One ml of P-2000 is added as an antifoaming agent to the jar fermenters only, then the vessels are sealed and sterilized at 120° C. and 1.06 kg/cm² for 60 to 90 minutes. The jars are inoculated with one (about 3% inoculum) flask, fermented for 72 to 120 hours at 27° C. and stirred at 1700 rpm with an air rate of one volume of air per volume of liquid per minute. The shake flasks (Fernbachs) are run at 150–200 cpm on a shaker at 28° C. and fermented for 72 to 120 hours. The fermenters are stopped and the contents extracted twice with one third to one half volume of a solvent such as methyl isobutyl ketone or n-butanol. The solvent layer is separated by aspiration or centrifugation, sparkled, and concentrated in vacuo to a viscous oil.

The bioactivity of the broth and subsequent recovery streams can be followed by HPLC or by using a strain of a filamentous fungi, e.g., *Byssochlamys fulva*. The components in the broth and recovery streams can also be visualized by chromatography on Artaltech silica gel FG (trademark) plates using neat ethyl acetate or chloroform-methanol 10:1 as the eldant. The developed plates are viewed under ultraviolet light at 254 run or are sprayed with vanillin reagent (e.g., 3 g vanillin in 75 ml of ethanol and 25 ml 85% phosphoric acid) and heated to 80° C. The compound appears as a gray blue spot. Extracts of the broth may be run in a Waters (trademark) analytical HPLC using a Zorbax CN (trademark) column and an isocratic system such as $H_2O$-acetonitrile 55:45.

Larger scale fermentations may be carried out by preparing shake flasks containing one liter of compound of formula I inoculum medium. The shake flask inoculum is fermented for 2 to 4 days at 28° C., and then used to inoculate a 50-gallon fermenter containing 25 gallons of production medium. The broth is harvested after running 3 to 5 days. The whole broth is extracted with ⅓ volume of methyl isobutyl ketone (MIBK) at natural pH, separated on an Alpha De Laval (trademark) separator and the solvent phase concentrated in vacuo to an oil. The term natural pH refers to the pH of the fermentation when stopped, or, if the pH is controlled, the pH at which the fermentation was run or maintained. The oil thus obtained may be processed as described below in Example 1.

Larger fermentere can be staged. A 100-gallon charge of compound of formula I seed medium is inoculated by side arm flask, run approx iraate ly 48 hours, then pumped aseptically into 1000 gallons of production medium.

The compound of the formula I inhibits the rotamase activity of human FK-binding protein. Functional biological activity in a human mixed lymphocyte reaction (MLR) may be demonstrated by standard procedures well known to those skilled in the art.

The immunosuppressant effect of the compound of the formula I may also be demonstrated by the following assay which measures the proliferation of mouse T lymphocytes stimulated with the combination of ionomycin plus PMA (phorbol myristate acetate). A positive sample in this assay will inhibit-T-cell proliferation, as indicated by reduced tritiated thymidine uptake.

Assay

Spleens from C57Bl/6 mice are taken under sterile conditions and gently dissociated in ice-cold RPMI 1640 (trademark) culture medium (GIBCO (trademark)) supplemented with 10% heat-inactivated fetal calf serum (GIBCO (trademark)). Cells are pelleted by centrifugation at 1500 rpm for 8 minutes. Contaminating red cells are removed by treating the pellet with ammonium chloride lysing buffer (GIBCO (trademark)) for 2 minutes at 4° C. Cold medium is added and cells are again centrifuged at 1500 rpm for 8 minutes. T lymphocytes are then isolated by separation of the cell suspension on nylon wool columns as follows: Nylon wool columns are prepared by packing approximately 4 grams of washed and dried nylon wool into 20 ml plastic syringes. The columns are sterilized by autoclaving at 120° C. for 30 minutes. Nylon wool columns are wetted with warm (37° C.) culture medium and rinsed with the same medium. Washed spleen cells resuspended in warm medium are slowly applied to the nylon wool. The columns are then incubated in an upright position at 37° C. for 1 hour.

Non-adherent T lymphocytes are eluted from the columns with warm culture medium and the cell suspensions are spun as above.

Purified T lymphocytes are resuspended at $10^6$ cells/ml in complete culture medium composed of RPMI 1640 (trademark) medium with 10% heat-inactivated fetal calf serum, 100 mM glutamine, 1 mM sodium pyruvate, 20 82 m 2-mercaptoethanol and 50 μg/ml gentamicin. Ionomycin is added at 250 ng/ml and PMA at 10 ng/ml. The cell suspension is immediately distributed into 96-well flat-bottom microculture plates (Costar (trademark)) at 100 82 l/well. Control (cyclosporin) medium or sample to be tested are then added in triplicate wells at 10 82 l/well. The culture plates are then incubated at 37° C. in a humidified atmosphere of 5% $CO_2$-95% air for 44 hours. The proliferation of T lymphocytes is assessed by measurement of tritiated thyroidins incorporation. After 44 hours of culturing, the cells are pulse-labelled with 2 Ci/well of tritiated thymidine (New England Nuclear (trademark)). After another 4 hours of incubation, cultures are harvested on glass fiber filters using a multiple sample harvester. Radioactivity of filter discs corresponding to individual wells is measured by standard liquid scintillation counting method (Beta plate counter). Mean counts per minute of replicate wells are calculated and the results expressed as percent inhibition of tritiated thymidine uptake (proliferation) as follows:

$$\% \text{ Inhibition} = 100 - \frac{\text{Mean } cpm \text{ sample tested}}{\text{Mean } cpm \text{ control medium}} \times 100.$$

The compound of the formula I has immunosuppressive activity and is therefore useful for the treatment and prevention of the transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosus, hashimoto's thyroidiris, multiple sclerosis, myasthenia gravis and type I diabetes. The compound also has antimicrobial activity and is useful in treating infectious diseases caused by pathogenic filamentus fungal organisms.

The pharmaceutical compositions of the present invention can be used in the form of a pharmaceutical preparation, for example, in solid, semi-solid or liquid form, which contains a compound of the formula I as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semi-solid, or liquid form, and in addition auxiliary, stabilizing, thickening and coloring agents and perfumes may be used. For applying such pharmaceutical compositions to a human, it is preferable to apply the compositions by parenteral or oral administration.

While the dosage of therapeutically effective amount of the compound of formula I depends upon the age and condition of each individual patient to be treated, a daily dose (calculated on the basis of a 70 kg man) of about 0.01 to about 1000 mg, preferably about 0.1 to about 500 mg and more preferably about 0.5 to about 100 mg of the active ingredient is generally given for treating transplantation rejection or the diseases referred to above, and an average single dose of about 0.5 mg, 1 mg, 5 mg, 10 mg, 50 mg, 100 mg, 250 mg or 500 mg is generally administered.

The following examples are given for the purpose of illustrating the present invention and should not be construed as being limitations on its scope.

EXAMPLE 1

Fermentation of N927-101

The organism N927-101 was isolated from a soil sample collected in Misumitown, Yamaguchi Prefecture, Japan.

A. Microtiter Fermentation

A sample of N927-101 colony on an agar-plate was inoculated into a seed medium W (2.5 ml) containing glucose (1 g), dextrin, polArpeptone (5 g/l), yeast extract (5 g/l), beef extract (3 g/l) and $CaCO_3$ (4 g/l) -in a 24-well microtiter plate and cultured at 28° C. for 3 days on a rotary shaker with 7-cm throw at 200 rpm. The seed culture (0.15–0.3 ml) thus obtained was inoculated to a production medium (3 ml) containing glucose (10 g/l), corn starch (20 g/l), NZ amine type-A (5 g/l), yeast extract 5 (g/l), wheat embryo (5 g/l), $COCl_2 \cdot H_2O$ (0.001 (g/l) and $CaCO_3$ (4 g/l) in a 24-well microtiter plate and cultured under the same conditions as the above seed culture except that the fermentation was 4 days.

The fermentation broth thus obtained was applied to a TLC (thin layer chromatography) plate (Kieselgel $60F_{254}$, E. Merck (trademark) 20×20 cm) and developed by $CHCl_3$: $CH_3OH$ (9:1). After the solvent was removed, the TLC plate was placed in a bioplate (28×44 cm) and overlayed by 300 ml of malt yeast agar (malt extract 20 g, yeast extract 4 g, agar 20 g in 1,000 ml) seeded with *Byssochlamys fulva*. The bioplate was incubated at 28° C. for 48 hours. At least two compounds were detected as the inhibition zones against the test organism with $R_f$ values of 0.30 and 0.55.

B. Flask Fermentation

In order to determine whether the compounds produced by the N927-101 colony where the same as known compounds, flask fermentation was carried out. A seed culture (100 ml) inoculated with 0.5 ml of frozen seed-culture from the microtiter fermentation was femented as described above and then 5 ml were used to prepare 100 ml of a main culture which was fermented as described above. 150 ml of the resulting fermentation broth was extracted with 100 ml of ethyl acetate (EtOAc). The EtOAc solution was concentrated to dryness. The residue was dissolved in 2 ml of acetone and submitted to TLC-bioautography. The TLC-bioautography with *Byssochlamys fulva* indicated that two FK-related compounds were reproduced. One of them having the Rf value of 0.55 was identical to FK-520 based on the HPLC analysis (Zorbax CN, Dupont (trademark) column: 4.6 mm×25 cm; eluent: 55% water/45% acetonitrile; flow rate: 1 ml/min; detection: UV 214 nm). Another compound with the Rf value of 0.30 was novel.

C. Mini-jar Fermentation

In order to isolate the novel compound and determine the structure, mini-Jar fermentation was carried out. A first seed culture was prepared by inoculating 100 ml of medium with 5 ml of frozen seed culture from the shake-flask fermentation. The medium (WGB medium) comprised water, glucose (20 g/l), polypeptone (5 g/l), yeast extract (5 g/l), beef extract-(3 g/l), wheat gluten (5 g/l), blood meal (3 g/l), and $CaCO_3$ (4 g/l). The culture was maintained at 28° C. for four days with rotation at 200 rpm.

Second seed cultures were prepared by inoculating 150 ml of WGB medium with 7.5 ml of the fermented first seed culture. The culture was maintained at 28° C. for three days with rotation at 200 rpm and aeration at 1.0 volume/volume/minute.

Main cultures were prepared in five 6-liter mini-jars by inoculating 3 liters of medium in each jar with 150 ml of the second seed culture. The medium (IT-2 medium) comprised glucose (10 g/l), dextrin (20 g/l), wheat gluten (10 g/l), corn steep liquor (5 g/l), polypeptone (1 g/l), $(NH_4)_2SO_4$ (1 g/l), $CaCO_3$ (4 g/l) and $COCl_2.6H_2O$ (0.001 g/l).

The whole mini-jar fermentation broth (15 1) was freeze-dried and the solid (397 g) was extracted with two 5-liter portions of 70% aqueous acetone and concentrated to 2.5 1 of aqueous suspension. The suspension was extracted with two 2-liter portions of methyl isobutyl ketone and the combined extract was concentrated to oily residue. A small amount of ether (100 ml) was added to the oily residue to give a precipitate. After collecting the precipitate (2.8 g), the ether solution was concentrated and 100 ml of n-hexane was added to yield 1.7 g of gum-solid. The 2.8 and 1.7 g gum solids were combined and applied to a 120 g fine mesh silica gel column which was developed with i L of 3:1 hexanes/ethyl acetate, followed by 1 L of 2:1 hexanes/ethyl acetate, 1 L of 1:1 hexanes/ethyl acetate, 1 L of 2:1 ethyl acetate/hexanes and finally by 2 L of ethyl acetate to yield 25 mg of FK-520 and 125 mg of a mixture of FK-520 and a novel compound. This mixture was applied to a 10 g fine mesh silica gel column which was eluted with 200 ml of chlorofom followed by 200 ml of chloroform with 2% methanol, 200 ml of chloroform with 5% methanol, and finally 100 ml of chloroform with 10% methanol to yield 10 mg of the new compound. This was further purified on a I g $C_{18}$ column developed with methanol and water in a ratio of 4/1 to yield 4 mg of the novel compound later found to have the formula I.

EXAMPLE 2

Large Scale Flask Fermentation

Shake flasks containing 80 ml of ATCC 172 medium were inoculated and fermented for 3 to 4 days at 28° C., then 10 ml was used to inoculate a 2.8 liter Fernbach flask containing one liter of ATCC 172 medium. The fermenter, after running 3 to 5 days, was harvested.

Figure 2:
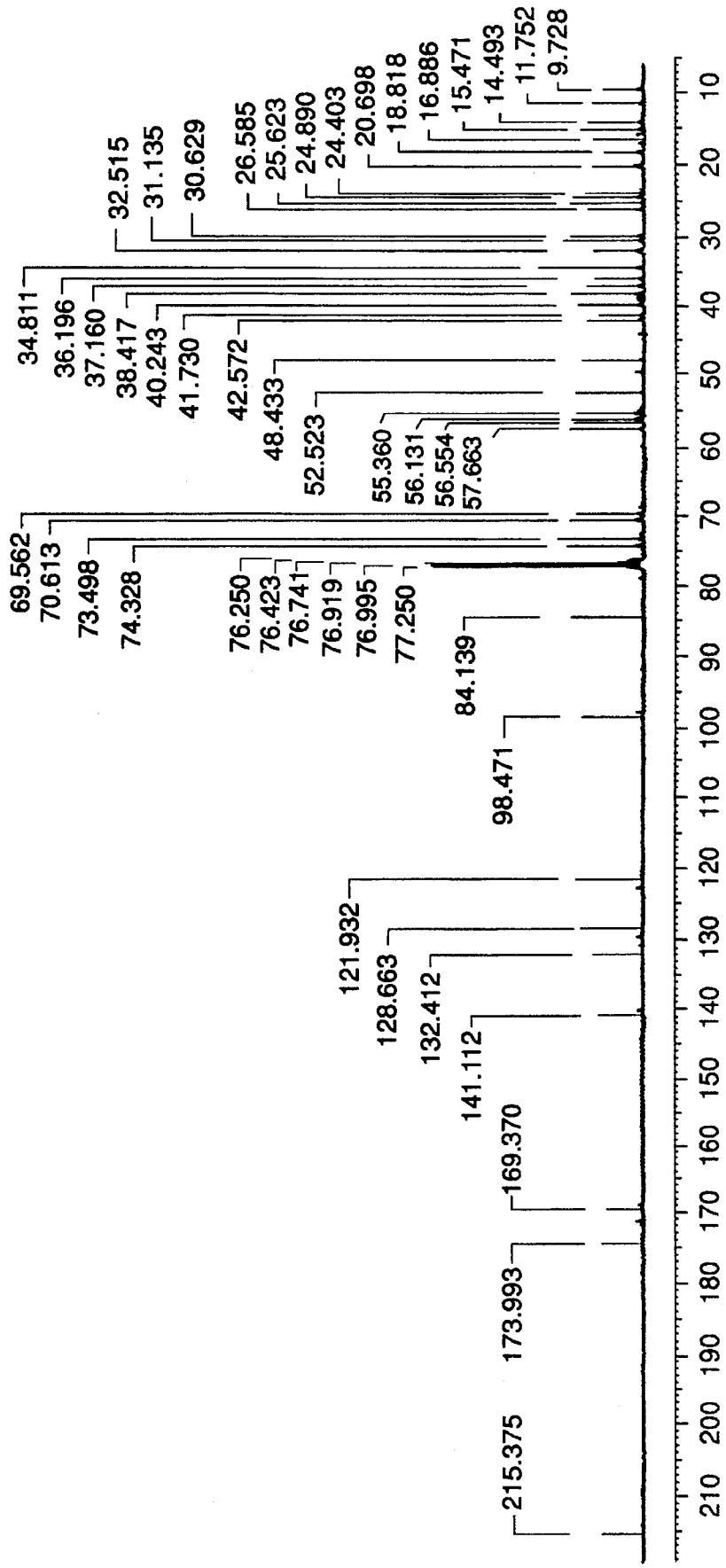
FIG. 2 is the carbon NMR spectrum in CDCl₃ of C₉-desoxo-FK- 520.

47 liters of N927-101 broth was extracted with methyl isobutyl ketone (MIBK) at natural pH. The MIBK phase was separated and concentrated in vacuo to an oil. The oil was defatted using acetonitrile and hexanes to give 4.0 g of a dark viscous liquid. This residue was chromatographed on 128 g of fine mesh silica gel which was pre-equilibrated with hexanes and ethyl acetate (1:1). The column was developed with 1 L of 1:1 ethyl acetate/hexanes, followed by 1 L of 2:1 ethyl acetate/hexanes, 1 L of 4:1 ethyl acetate/hexanes and finally by 1.5 L of ethyl acetate to yield 290 mg of a yellow oil. This mixture was then chromatographed on a second fine mesh silica gel column which was pre-equilibrated with chloroform and developed with 200 ml of chloroform, followed by 500 ml of chloroform with 1% methanol and then with 500 ml of chloroform with 2% methanol to yield 125 mg of an oil. This oil was chromatographed on Baker (trademark) $C_{18}$ bulk packing for flash chromatography using methanol and water (3:1) to give 42 mg of product. Proton NMR and carbon NMR-(see FIGS. 1 and 2) indicated the chemical structure of the product to be as shown in formula I. The molecular weight of 777, as determined by FAB (fast atom bombardment) mass spectroscopy, is consistent with the formula I.

We claim:

1. A process for preparing a compound of the formula

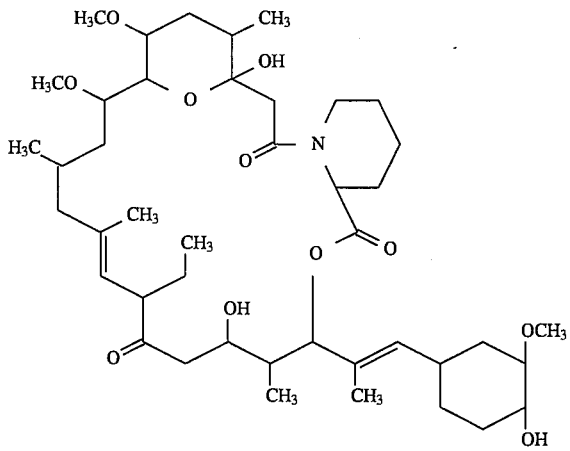

comprising fermenting an organism having all of the identifying characteristics of *Streptomyces braegensis* subsp. *pulcherrimus* Huang subsp. nov., ATCC 55150, under aerobic conditions in an aqueous medium containing a carbon source and a nitrogen source and recovering said compound of formula I by extracting the fermentation broth with an organic solvent at a pH of about 4.0 to about 8.0.

2. A process according to claim 1, comprising fermenting the organism strain ATCC 55150 under aerobic conditions in an aqueous medium containing a carbon source and a nitrogen source and recovering said compound of formula I by extracting the fermentation broth with an organic solvent at a pH of about 4.0 to about 8.0.

3. A process according to claim 1, wherein said fermentation is conducted at a pH between about 4.0 and about 8.0.

4. A process according to claim 1, wherein said fermentation is conducted at a temperature from about 20° C. to about 40° C., for a period of time from about 50 hours to about 150 hours.

5. A process according to claim 4, wherein said fermentation is conducted at a temperature from about 24° C. to about 36° C. under submerged conditions with agitation and aeration on a medium containing a carbon source and a nitrogen source, one or more mineral salts containing trace metals and one or more buffering agents.

6. A biologically pure culture having all of the identifying characteristics of *Streptomyces braegensis* subsp. *pulcherrimus* Huang subsp. nov., ATCC 55150, and any mutant thereof capable of producing the compound of the formula

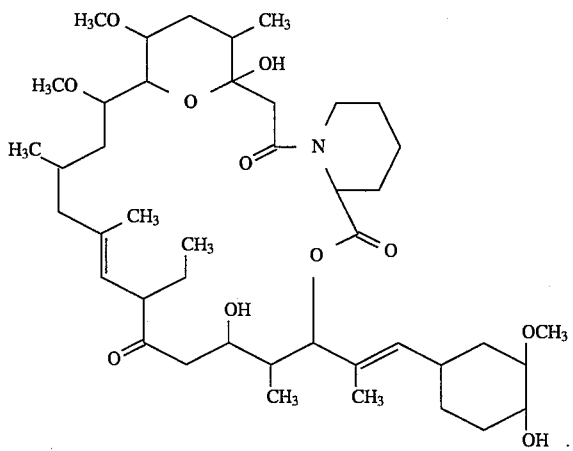

7. A biologically pure culture of *S. braegensis* subsp, *pulcherrimus* ATCC 55150 according to claim 6.

* * * * *